US00H002093H

(19) United States

(12) Statutory Invention Registration (10) Reg. No.: US H2093 H

Warner et al. (43) Published: Jan. 6, 2004

(54) INTRAVENOUS FLUID WARMING UNIT

(75) Inventors: Jeffrey P. Warner, Alexandria, VA (US); Stephen D. Knecht, Spokane, WA (US)

(73) Assignee: The United States of America as represented by the Secretary of the Air Force, Washington, DC (US)

(21) Appl. No.: 09/061,352

(22) Filed: Apr. 13, 1998

(51) Int. Cl.[7] ..... F24J 1/00; F24J 3/00

(52) U.S. Cl. ..... 126/263.07; 604/113; 604/408

(58) Field of Search ..... 604/113, 408; 126/263.01, 263.02, 263.03, 263.04, 263.05, 263.06, 263.07

(56) References Cited

U.S. PATENT DOCUMENTS

| | | | | |
|---|---|---|---|---|
| 4,804,367 A | | 2/1989 | Smith et al. | |
| 4,901,472 A | * | 2/1990 | Donohue et al. | 126/263 |
| 4,934,336 A | * | 6/1990 | White | 126/263 |
| 5,101,804 A | | 4/1992 | Cohn | |
| 5,263,929 A | | 11/1993 | Falcone et al. | |
| 5,295,964 A | * | 3/1994 | Gauthier | 604/113 |
| 5,611,329 A | * | 3/1997 | Lamensdorf | 126/263.07 |

* cited by examiner

*Primary Examiner*—Harold J. Tudor

(74) *Attorney, Agent, or Firm*—Fredric L. Sinder; Thomas L. Kundert

(57) ABSTRACT

A novel intravenous ("IV") warming unit warms and keeps warm intravenous fluid bags for use at remote sites under arctic conditions. The IV fluid warming unit is made of fabric cut and sewn to form a suitcase-like folding receptacle, or satchel. The satchel has four inside pockets along one inside surface and overlapping webbing on the other inside surface. Chemical heating pads are activated and placed inside the pockets and IV fluid bags placed under the webbing. When the satchel is closed, the chemical heating pads warm and keep warm the IV fluid bags. In use, the satchel is placed on top of the chest of a patient so that the satchel warms the patient from the outside while the warmed IV fluid warms the patient from the inside.

4 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

INTRAVENOUS FLUID WARMING UNIT

RIGHTS OF THE GOVERNMENT

The invention described herein may be manufactured and used by or for the Government of the United States for all governmental purposes without the payment of any royalty.

BACKGROUND OF THE INVENTION

The present invention relates generally to emergency medical procedures, and more specifically to maintaining intraveneous fluids at usable temperatures, particularly at remote sites under arctic conditions.

Intravenous ("IV") fluids must be kept at usable temperatures, generally above 98.6° F. This presents an unusually severe challenge at remote sites in artic conditions. In the past, emergency medical rescuers would try to keep IV fluids warm by putting bags of fluid inside their parkas and attempting to use their body heat to warm the fluids. This was ineffective in that it was difficult to keep the bags from falling out of the parkas and body heat is insufficient to warm the fluids to an ideal temperature of 110° F. Another problem was that once an IV is started and the IV bag is on a patient's chest, there is no longer a heat source for the fluid because the patient is already cold. Therefore, cold fluid is being delivered to a hypothermic patient, worsening his or her condition.

A commercial IV fluid warmer is available for about $300.00, but it requires external 120 volt power, which is generally unavailable in remote arctic regions. Another commercial IV fluid warmer is available for about $350.00 that is battery operated. Unfortunately, the extreme cold of arctic regions substantially reduces the performance of batteries, so much so that, for example, in the case of battery-powered radios, the problem of keeping those radios running is already so difficult that attempting to keep another battery-powered device in operation would be more trouble than it is worth. Not only does the extreme cold reduce the life of the batteries, but they are also prone to becoming cold soaked, rendering a radio useless.

This it is seen that there is a need for a self-powered IV fluid warmer that will successfully warm and keep warm bags of IV fluid at remote sites under arctic conditions.

It is, therefore, a principal object of the present invention to provide an IV fluid warming unit that warms rapidly and stays warm for a period of time sufficient to allow use of bags of IV fluid for patient care in extremely cold environments and that does not need an external power source.

It is a feature of the present invention that it warms and keeps warm several IV bags at the same time.

It is another feature of the present invention that it also provides warmth to the patient from the outside as IV fluid is being supplied to warm the patient from the inside.

It is an advantage of the present invention that it continues to warm spare IV bags as fluid is being supplied to a patient from one of the warmed IV bags.

It is another advantage of the present invention that it can be made at a very low cost.

These and other objects, features and advantages of the present invention will become apparent as the description of certain representative embodiments proceeds.

SUMMARY OF THE INVENTION

The present invention provides a fast and safe apparatus and method for warming and keeping warm bags of IV fluid at remote sites in arctic conditions. The unique discovery of the present invention is that a sealable satchel containing pockets for holding chemical heating pads and webbing for holding corresponding bags of IV fluid next to the pockets provides a fast and safe apparatus for warming and keeping warm bags of IV fluid for use at remote sites under arctic conditions.

Accordingly, the present invention is directed to a warmer for intravenous fluids, comprising a flexible satchel, including first and second generally rectangular sides, the sides connected along a mutual edge to form a folding seam for closing the two sides together, the two sides and the satchel having corresponding insides and outsides, hook and fabric reclosable fastening strips along at least a portion of the inside of the edges of the first and second sides for securing the satchel when closed, four pockets sewn onto the inside of the first side for holding four chemical heating pads, and web straps over the inside of the second side for holding in place four intravenous fluid bags.

The present invention is also directed to a more broadly described warmer for intravenous fluids, comprising a flexible satchel, including first and second sides, the sides connected along a portion of their edges to form a folding seam for closing the two sides together, the two sides and the satchel having corresponding insides and outsides, reclosable fastening strips along at least a portion of the inside of the edges of the first and second sides for securing the satchel when closed, a first holder attached to the inside of the first side for holding at least one self-powered heating unit, and a second holder attached to the inside of the second side for holding in place at least one intravenous fluid bag.

The present invention is further directed to a method for warming intravenous fluids, comprising the steps of providing a flexible satchel, the flexible satchel including first and second generally rectangular sides, the sides connected along a mutual edge to form a folding seam for closing the two sides together, the two sides and the satchel having corresponding insides and outsides, reclosable fastening strips along at least a portion of the inside of the edges of the first and second sides for securing the satchel when closed, pockets sewn onto the inside of the first side for holding one or more chemical heating pads, and web straps over the inside of the second side for holding in place one or more intravenous fluid bags, placing at least one activated chemical heating unit inside the pockets, placing at least one intravenous fluid bag under the web straps, and closing the first and second sides together to bring any chemical heating units into thermal contact with the intravenous fluid bags.

The present invention is still further directed to a more broadly described method for warming intravenous fluids, comprising the steps of providing a flexible satchel, the flexible satchel including first and second sides, the sides connected along a portion of their edges to form a folding seam for closing the two sides together, the two sides and the satchel having corresponding insides and outsides, reclosable fastening strips along at least a portion of the inside of the edges of the first and second sides for securing the satchel when closed, a first holder attached to the inside of the first side for holding at least one self-powered heating unit and a second holder attached to the inside of the second side for holding in place at least one intravenous fluid bag, placing at least one self-powered heating unit inside the first holder, placing at least one intravenous fluid bag inside the second holder, and closing the first and second sides together to bring any self-powered heating units into thermal contact with any intravenous fluid bags.

BRIEF DESCRIPTION OF THE DRAWINGS

The present invention will be more clearly understood from a reading of the following detailed description-in conjunction with the accompanying drawing wherein.

DETAILED DESCRIPTION

Figure 1:
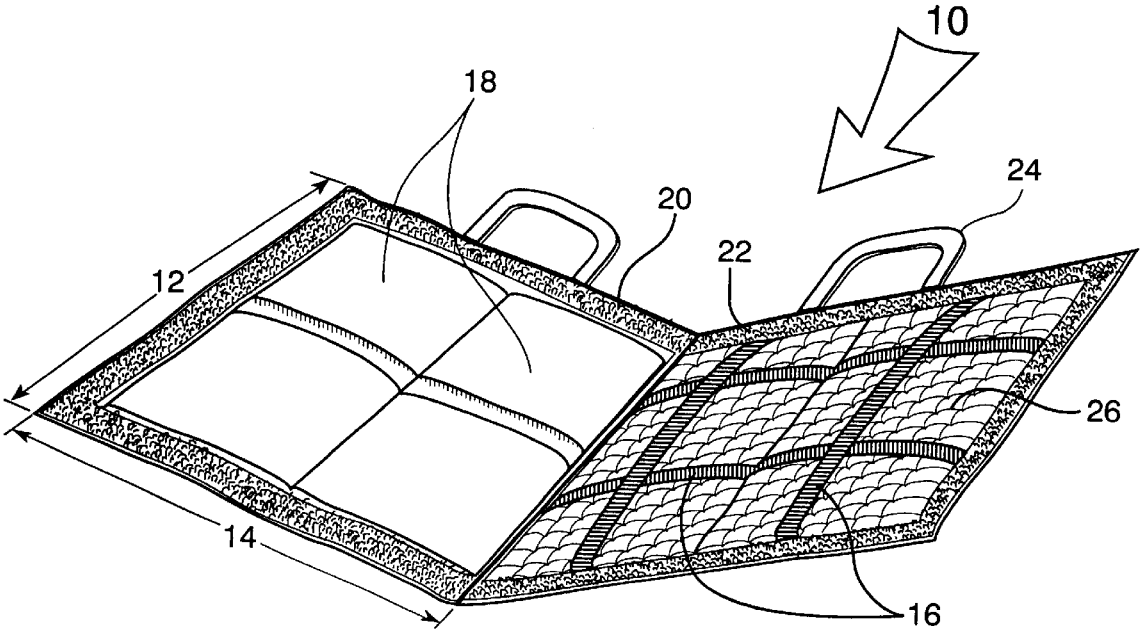
FIG. 1 is a perspective view of an intravenous fluid warming unit made according to the teachings of the present invention.

Referring now to FIG. 1 of the drawings, there is shown a perspective view of an intravenous fluid warming unit 10 in its open position. IV fluid warming unit 10 is made of nylon fabric cut and sewn to form a satchel, or suitcase-like folding receptacle. The dimensions of IV fluid warming unit 10 are, when folded, about eighteen inches along length 12 and about sixteen inches along length 14. IV fluid warming unit 10 includes four sets of overlapping nylon or elastic web straps 16 for holding four IV bags and four pockets 18 for holding four chemical heating pads. VELCRO strips 20 and 22 surround IV fluid warming unit 10 to secure it when closed. A pair of handles 24 are attached to one side of IV fluid warming unit 10. Insulation 26 is applied to one side of IV fluid warming unit 10 to help prevent cold reaching the IV bags though the outside of IV fluid warming unit 10. The other side of IV fluid warming unit 10 is not insulated so that warmth from the chemical heating pads will help warm a patient when IV fluid warming unit 10 is placed on top of the patient's chest.

Chemical heating pads are heating pads that supply heat from a chemical reaction and do not require a separate power source. Preferred chemical heating pads are water-actuated. Such water-actuated heating pads are commonly available based on a variety of different exothermic chemical reactions. A preferred example of such a water-actuated chemical heating pad is a chemical heating pad used by the military. They are manufactured by Truetech, Inc., in Riverhead, N.Y., and have been available under National Stock Number ("NSN") 6530-00-786-4273. These chemical heating pads contain a white powder and, after introduction of water and then mixing, will produce heat for up to eight hours unaffected by arctic conditions. A particular advantage of these chemical heating pads is that they are reusable. Another possible chemical heating pad for use with the present invention, although not reusable, would be a self-powered heating pad commonly available for skiing and other winter sports which uses rapid oxidation, or rusting, of iron wool or iron shavings as the exothermic chemical reaction.

To use, IV bags should be first prepped to remove all air from inside the bags. The bags should then be put into infusion cuffs (a standard unit similar to a blood pressure cuff for pressurizing IV bags to force IV fluid out of the bags under pressure) and secured or strapped down under web straps 16.

As soon as it is suspected that warmed IV fluid will be needed, the chemical heating pads should be activated by pouring, in the case of NSN 6530-00-786-4635 bags, two tablespoons of water into their openings and kneading the pads until they begin to heat. The chemical heating bags should then each be placed inside their individual pockets 18 and IV fluid warming unit 10 folded closed using the VELCRO strips 20 and 22. After a patient is inside a sleeping bag, IV fluid warming unit 10 is placed on the patient's chest and delivery of IV fluid from one of the IV bags begun. The IV tubing will extend between VELCRO strips 20 and 22, which will close around the tubing. As little of the IV tubing extending from an IV bag to the patient should be exposed as possible to avoid cooling of the IV fluid as it passes through the exposed tubing. The infusion cuff is then inflated to force IV fluid into the patient's vein since gravity is not being used.

IV fluid warming unit 10 will keep IV fluids at approximately 100–110° F. for up to six to eight hours, depending on the outside temperature. The preferred chemical heating pads are reusable and are generally unaffected by extreme arctic conditions.

The disclosed intravenous fluid warming unit successfully demonstrates the advantages of a folding satchel for holding self-powered chemical heating units in contact with IV bags for use in extremely cold environments. Although the disclosed invention is specialized, its teachings will find application in other areas where medical devices need to be brought up to and kept at a particular temperature or in another physical state in hostile environments.

Those with skill in the art of the invention will readily see other means than the described pockets and webbing for holding inside the satchel heating pads and IV bags. It is understood, therefore, that those and other modifications to the invention may be made, as might occur to one with skill in the field of this invention, within the scope of the appended claims. All embodiments contemplated have not been shown in complete detail. Other embodiments may be developed without departing from the spirit of this invention or from the scope of the claims.

We claim:

1. A warmer for intravenous fluids, comprising a flexible satchel, including:

(a) first and second generally rectangular sides, the sides connected along a mutual edge to form a folding seam for closing the two sides.-together-, the two sides and the satchel having corresponding insides and outsides;

(b) hook and fabric reclosable fastening strips along at least a portion of the inside of the edges of the first and second sides for securing the satchel when closed;

(c) four pockets sewn onto the inside of the first side for holding four chemical heating pads; and, (d) web straps over the inside of the second side for holding in place four intravenous fluid bags.

2. A warmer for intravenous fluids, comprising a flexible satchel, including:

(a) first and second sides, the sides connected along a portion of their edges to form a folding seam for closing the two sides together, the two sides and the satchel having corresponding insides and outsides;

(b) reclosable fastening strips along at least a portion of the inside of the edges of the first and second sides for securing the satchel when closed;

(c) a first holder attached to the inside of the first side for holding at least one self-powered heating unit; and, (d) a second holder attached to the inside of the second side for holding in place at least one intravenous fluid bag.

3. A method for warming intravenous fluids, comprising the steps of:

(a) providing a flexible satchel, the flexible satchel including:

(i) first and second generally rectangular sides, the sides connected along a mutual edge to form a folding seam for closing the two sides together, the two sides and the satchel having corresponding insides and outsides;

(ii) reclosable fastening strips along at least a portion of the inside of the edges of the first and second sides for securing the satchel when closed;

(iii) pockets sewn onto the inside of the first side for holding one or more chemical heating pads; and, (iv) web straps over the inside of the second side for holding in place one or more intravenous fluid bags;

(b) placing at least one activated chemical heating unit inside the pockets;

(c) placing at least one intravenous fluid bag under the web straps; and, (d) closing the first and second sides together to bring any chemical heating units into thermal contact with the intravenous fluid bags.

4. A method for warming intravenous fluids, comprising the steps of:

(a) providing a flexible satchel, the flexible satchel including:

(i) first and second sides, the sides connected along a portion of their edges to form a folding seam for closing the two sides together, the two sides and the satchel having corresponding insides and outsides;

(ii) reclosable fastening strips along at least a portion of the inside of the edges of the first and second sides for securing the satchel when closed;

(iii) a first holder attached to the inside of the first side for holding at least one self-powered heating unit; and, (iv) a second holder attached to the inside of the second side for holding in place at least one intravenous fluid bag;

(b) placing at least one self-powered heating unit inside the first holder;

(c) placing at least one intravenous fluid bag inside the second holder; and, (d) closing the first and second sides together to bring any self-powered heating units into thermal contact with any intravenous fluid bags.

* * * * *